United States Patent [19]

Kikuchi et al.

[11] Patent Number: 5,064,642
[45] Date of Patent: Nov. 12, 1991

[54] COMPOSITION FOR EXTERNAL APPLICATION

[75] Inventors: Yoko Kikuchi, Toride; Yukihiro Ohashi, Haga; Yuji Suzuki, Sakura; Toshiyuki Suzuki, Ichikawa, all of Japan

[73] Assignee: Kao Corporation, Tokyo, Japan

[21] Appl. No.: 582,150

[22] Filed: Sep. 13, 1990

[30] Foreign Application Priority Data

Sep. 13, 1989 [JP] Japan ................................. 1-238066

[51] Int. Cl.$^5$ ..................... A61K 7/048; A61K 7/021; A61K 7/06; A61K 7/04
[52] U.S. Cl. ........................................ 424/61; 424/63; 424/64; 424/70; 514/789; 585/21
[58] Field of Search ................ 424/63, 64, 61, 70; 514/766, 789; 585/1, 2, 21

[56] References Cited

U.S. PATENT DOCUMENTS 2,070,915  2/1937  Omohundro et al. .......... 514/784 X
4,740,370  4/1988  Foryniarz et al. ..................... 424/61

FOREIGN PATENT DOCUMENTS 0907457  3/1946  France .
0996017  12/1951  France .

Primary Examiner—Thurman K. Page
Assistant Examiner—Susan S, Rucker
Attorney, Agent, or Firm—Oblon, Spivak, McClelland, Maier & Neustadt

[57] ABSTRACT

A composition for external application comprising a tricyclic saturated hydrocarbon represented by formula (I) is disclosed.

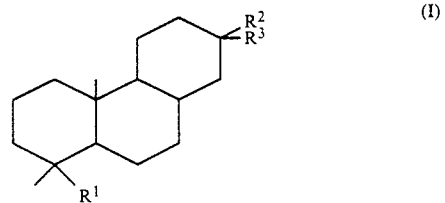

wherein $R^1$ and $R^2$ may be the same or different and independently represents a hydrogen atom or a methyl group and $R^3$ represents an alkyl group having 2–3 carbon atoms. The compositions for external application of the present invention exhibit an excellent moisture-retention effect and impart moistened feel without sliminess and irritation to the skin. They are thus useful as skin cosmetics, hair cosmetics, medical compositions for external application, and the like.

1 Claim, No Drawings

COMPOSITION FOR EXTERNAL APPLICATION

BACKGROUND OF THE INVENTION

1. Field of the Invention

This invention relates to a composition for external application, for example, a skin and hair cosmetic composition and a external medical composition, and more particularly, to a composition for external application exhibiting an excellent moisture-retention effect and imparting moistened feel without sliminess and irritation to the skin.

2. Description of the Background Art

A proper amount of water generally contained in the outermost crust of the skin and hair is indispensable for maintaining flexibility, softness, protective functions of the skin and hair. When the water content in the skin decreases, for example, the skin turns into, namely, dry skin, in which its flexibility and protective function are lost, resulting in a cause of various troubles. Whereas, sebum is known to have an important function to prevent the excessive loss of water from the outermost crust of the skin and hair and consequently can avoid the above-mentioned troubles.

In this regard, various oils including squalane which is a component involved in the skin, have conventionally been used as a component for cosmetics and the like to prevent the skin and hair from excessive drying.

However, external compositions containing these oils, e.g. cosmetics and the like, have disadvantages that they generally exhibit high sliminess when applied and give unacceptable feel upon use. On the other hand, hydrocarbons of low melting points are known as a less slimy oil component, however, they inevitably impart irritation to the skin under closed conditions.

Compositions for external application exhibiting an excellent moisture-retention effect without sliminess and irritation to the skin have therefore been desired.

In view of this situation, the present inventors have undertaken extensive studies to solve the above-mentioned problems. As a result, the inventors have found that a composition for external application comprising a specific tricyclic saturated hydrocarbon could exhibit an excellent moisture-retention effect, impart moistened feel, and have high safety without sliminess and irritation to the skin. This finding has led to the completion of the invention.

SUMMARY OF THE INVENTION

Accordingly, an object of this invention is to provide a composition for external application comprising a tricyclic saturated hydrocarbon represented by the following formula (I):

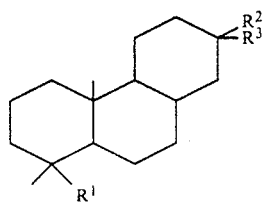

(I)

wherein $R^1$ and $R^2$ may be the same or different and independently represents a hydrogen atom or a methyl group and $R^3$ represents an alkyl group having 2-3 carbon atoms.

Since the compound of formula (I) is contained in rosin and the like in a small amount, it is not impossible to obtain the substance from rosin or the like by isolation and refining. It is, however, desirable to synthesize the compound of formula (I) from abietic acid, pimaric acid, or the like according to a conventional method [*J. Org. Chem.*, 34(6), 1562, (1962); *Sb. Vys. Sk. Chem.-Technol. Praze, Technol. Paliv,* D44, 125, (1981); *Tetrahedron*, 25, 1335, (1969)]. An exemplary method for synthesizing the compound of formula (I) will now be explained using preferable examples of the compound of formula (I); abietane, pimarane, norabietane, and norpimarane.

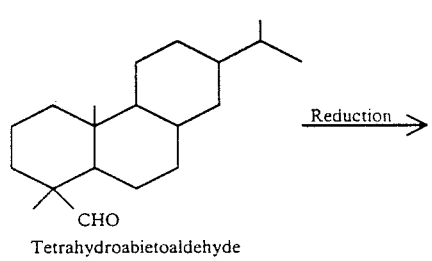

Tetrahydroabietoaldehyde

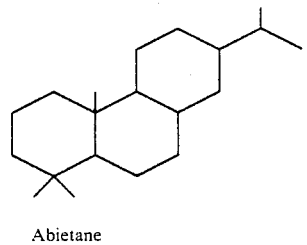

Abietane

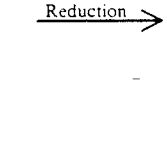

Tetrahydropimaraldehyde

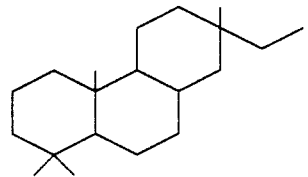

Pimarane

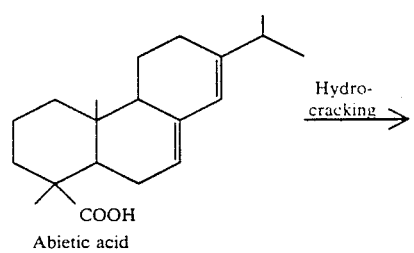

Abietic acid

-continued

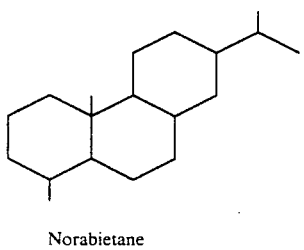

Norabietane

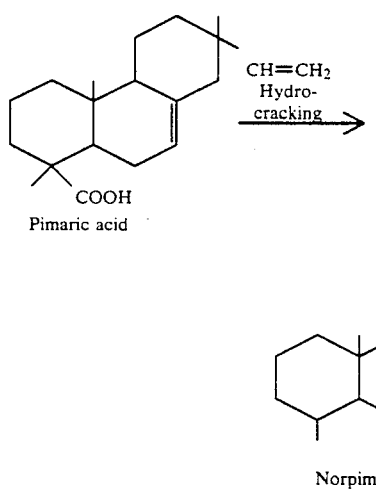

Specifically, abietane and pimarane can be produced by the Wolff-Kishner reduction of tetrahydroabietoaldehyde and of tetrahydropimaraldehyde, respectively. Norabietane and norpimarane can be produced by hydrocracking of abietic acid and pimaric acid, respectively, in the presence of a hydrogenation catalyst such as Raney nickel or the like.

The tricyclic saturated hydrocarbons of formula (I) thus obtained are a liquid having relatively low viscosity at normal temperature, and have good chemical stability and low irritation to the skin. They are thus useful as an oil component of compositions for external application. The amount of the compound of formula (I) to be formulated in the composition is determined depending on a kind of products, e.g. medicines for external application, cosmetics, or the like. Generally, the compound of formula (I) is incorporated in the composition in an amount of 0.1–80% by weight, and preferably 1–50% by weight.

Any carriers acceptable for external application which are ordinarily used in cosmetics or medicines can be used in the composition of the present invention as a vehicle of the above-mentioned essential components. Such carriers include, for example, water, medical components, various kinds of cosmetic oils, surface active agents, humectants, UV-absorbers, chelating agents, pH adjusting agents, antiseptics, thickeners, pigments, perfumes, and the like.

The compositions of the present invention can be formulated into any forms of preparations such as oil-type, water-type, emulsion-type or the like, and are particularly suitable for the skin or hair cosmetics which require a moisture-retention effect to care chapped skin or damaged hair.

The compositions for external application of the present invention exhibit an excellent moisture-retention effect and impart moistened feel without sliminess and irritation to the skin. They are thus useful as skin cosmetics, hair cosmetics, medical compositions for external application, and the like.

Other features of the invention will become apparent in the course of the following description of the exemplary embodiments which are given for illustration of the invention and are not intended to be limiting thereof.

EXAMPLES

Synthetic Example 1

Synthesis of Norabietane 45 g (0.15 mol) of abietic acid, 100 ml of cyclohexane, and 5 g of Raney nickel as a catalyst were charged in a 500 ml revolving autoclave and reacted at 270° C. under a hydrogen pressure of 150 Kg/cm$^2$ for 7 hours. After the reaction, the catalyst was removed from the reaction mixture by filtration and the filtrate was distilled under reduced pressure to obtain 20 g of target norabietane (yield: 51%).

Boiling Point: 135°–145° C./0.05 Torr
MS: M$^+$ 262

Synthetic Example 2

Synthesis of Norpimarane

Norpimarane was produced in the same manner as in Synthetic Example 1 except that pimaric acid was used instead of abietic acid (yield: 45%).

Boiling Point: 140°–145° C./0.05 Torr
MS: M$^+$ 262

Synthetic Example 3

Synthesis of Abietane 36 g (0.125 mol) of tetrahydroabietoaldehyde, 1 litter of triethylene glycol, 500 ml of anhydrous NH$_2$NH$_2$, and 150 g of NH$_2$NH$_2$.2HCl were charged into a 3 1 flask equipped with a stirrer and agitated at 120°–140° C. for 14 hours. After having been cooled to room temperature, the mixture to which 200 g of KOH had been added was heated to 200° C. over 3 hours. The mixture was further kept heated with stirring at this temperature for 3 hours. To the reaction mixture was added saline followed by extracting with hexane and distilling under reduced pressure to produce 26 g of target abietane (yield: 75%).

Boiling Point: 148°–152° C./0.05 Torr
MS: M$^+$ 276

Synthetic Example 4

Synthesis of Pimarane

Pimarane was produced in the same manner as in Synthesis Example 3 except that tetrahydropimaraldehyde was used instead of tetrahydroabietoaldehyde (yield: 68%).

Boiling Point: 150°–156° C./0.05 Torr
MS: M$^+$ 276

Example 1

Emulsion cosmetics having the formulation shown in Table 1 were prepared according to the preparation method explained below, and the feeling upon use were sensuously evaluated by expert panelists. The results are shown in Table 1.

Preparation Method

Components (1)–(6) in Table 1 were mixed and heated, and then component (7) was added under stirring. The mixture was cooled with stirring to obtain a cosmetic composition.

TABLE 1

| Component | Invention Composition 1 | 2 | 3 | 4 | % by weight Comparative Composition |
|---|---|---|---|---|---|
| (1) Norabietane | 10.0 | — | — | — | — |
| (2) Abietane | — | 10.0 | — | — | — |
| (3) Norpimarane | — | — | 10.0 | — | — |
| (4) Pimarane | — | — | — | 10.0 | — |
| (5) Squalane | — | — | — | — | 10.0 |
| (6) Polyoxyethyleneoleyl ether (20 E.O.) | 2.0 | 2.0 | 2.0 | 2.0 | 2.0 |
| (7) Purified water | Balance | | | | Balance |
| Feel upon use | | | | | |
| Moistened feel | found | found | found | found | found |
| Sliminess | none | none | none | none | none |
| Fresh feel | found | found | found | found | none |

Experimental Example

Irritation Test

10% by weight of the tricyclic saturated hydrocarbon of the present invention to be used for Invention Compositions 1–4 was dissolved in a liquid paraffin to prepare a test sample. The test sample was applied to a clipped and shaved lateral region of white Hartley guinea pigs (5 pigs per one group) once in a day for four consecutive days. A cutireaction of the lateral region was observed one day after the final application of the test sample and evaluated by the following criteria. The results are shown in Table 2.

Evaluation Standard point 0: no reaction
point 1 slight or disseminated erythema was observed
point 2: clear erythema was observed
point 3: erythema with edema was observed
point 4: scabrities or cutaneous necrosis was observed

TABLE 2

| Test sample | Average evaluation point |
|---|---|
| Norabietane | 0 |
| Abietane | 0 |
| Norpimarane | 0.2 |
| Pimarane | 0 |
| Invention Composition | |
| No. 1 | 0 |
| No. 2 | 0 |
| No. 3 | 0 |
| No. 4 | 0 |
| Liquid paraffin (reagent) | 0.2 |
| n-dodecane | 2.8 |
| Pristane | 3.0 |

Example 2

Moisturizing Lotion

A moisturizing lotion having the following formulation was prepared according to the process explained below.

| <Formulation> | % by weight |
|---|---|
| (1) Abietane | 1.0 |
| (2) Polyoxyethyleneoleyl ether (20 E.O.) | 1.5 |
| (3) Glycerol | 5.0 |
| (4) 1,3-butanediol | 5.0 |
| (5) Polyethylene glycol 1500 | 1.5 |
| (6) Ethanol | 10.0 |
| (7) Methyl parabene | 0.1 |
| (8) Perfume | q.s. |
| (9) Citric acid | q.s. |
| (10) Sodium citrate | q.s. |
| (11) Purified water | Balance |
| Total | 100.0 |

Preparation Method

To components (1), (2), (6), and (8) which had been homogeneously mixed, a mixture of components (3)–(5), (7), and (9)–(11) was added and stirred to prepare an almost homogeneous solution.

The moisturizing lotion thus obtained exhibited excellent moistened and decent feel without sliminess, providing an excellent moisture-retention effect and fresh feel upon use.

Example 3

Milky Lotion

A milky lotion having the following formulation were prepared according to the process explained below.

| <Formulation> | % by weight |
|---|---|
| (1) Norabietane | 10.0 |
| (2) Cethanol | 0.5 |
| (3) Vaseline | 1.0 |
| (4) Polyoxyethyleneoleyl ether (20 E.O.) | 2.0 |
| (5) Stearic acid | 2.0 |
| (6) Glycerol | 3.0 |
| (7) Dipropylene glycol | 5.0 |
| (8) Triethanolamine | 1.0 |
| (9) Ethyl parabene | 0.1 |
| (10) Methyl parabene | 0.2 |
| (11) Perfume | q.s. |
| (12) Purified water | Balance |
| Total | 100.0 |

Preparation Method

Components (1)–(5) were mixed and dissolved by heating and kept at 70° C. Components (6)–(10) and (12) were also mixed and dissolved by heating at 70° C. The former mixture was added to the latter and emulsified using an emulsification apparatus. An emulsion obtained was cooled to 40° C. while stirring. Component (11) was added to the emulsion and homogeneously mixed. The mixture was cooled by a heat-exchanger finally to 30° C. to prepare a milky lotion.

The milky lotion thus obtained exhibited excellent moistened and decent feel without sliminess, providing an excellent moisture-retention effect and fresh feel upon use.

Example 4

Moisturizing Cream

A moisturizing cream having the following formulation was prepared according to the process explained below.

| <Formulation> | % by weight |
| --- | --- |
| (1) Norabietane | 8.0 |
| (2) Norpimarane | 2.0 |
| (3) Paraffin wax | 2.0 |
| (4) Cetyl 2-ethylhexanoate | 5.0 |
| (5) Lanolin | 5.0 |
| (6) Bees wax | 2.0 |
| (7) Stearyl alcohol | 4.0 |
| (8) Glycerol monostearate (autoemulsion-type) | 1.5 |
| (9) Polyoxyethylenesorbitan monoolate (20 E.O.) | 1.0 |
| (10) Glycerol | 5.0 |
| (11) 70% aqueous sorbitol | 10.0 |
| (12) Ethyl parabene | q.s. |
| (13) Methyl parabene | q.s. |
| (14) Perfume | q.s. |
| (15) Purified water | Balance |
| Total | 100.0 |

Preparation Method

Components (1)–(9) were dissolved with heating and kept at 70° C. Components (10)–(13) and (15) were also mixed with heating at 70° C. The former mixture was added to the latter and the mixture was emulsified using an emulsification apparatus. An emulsion obtained was cooled to 40° C. while stirring. Component (14) was added to the emulsion and homogeneously mixed. The mixture was cooled by a heat-exchanger finally to 30° C. to prepare a moisturizing cream.

The moisturizing cream thus obtained exhibited excellent moistened feel without sliminess, providing an excellent moisture-retention effect and fresh feel upon use.

Example 5

Cold Cream

A cold cream having the following formulation was prepared according to the process explained below.

| <Formulation> | % by weight |
| --- | --- |
| (1) Norabietane | 28.0 |
| (2) Pimarane | 2.0 |
| (3) Bees wax | 5.0 |
| (4) Cetaceum | 3.0 |
| (5) Cetyl 2-ethylhexanoic acid | 10.0 |
| (6) Cetanol | 1.0 |
| (7) Glycerol monostearate (autoemulsion-type) | 7.0 |
| (8) Polyoxyethylenesorbitan monoolate (20 E.O.) | 2.0 |
| (9) Glycerol | 5.0 |
| (10) Triethanolamine | 0.3 |
| (11) Ethyl parabene | q.s. |
| (12) Methyl parabene | q.s. |
| (13) Perfume | q.s. |
| (14) Purified water | Balance |
| Total | 100.0 |

Preparation Method

Components (1)–(8) were dissolved with heating and kept at 70° C. Components (9)–(12) and (14) were also mixed with heating at 70° C. The former mixture was added to the latter and the mixture was emulsified using an emulsification apparatus. An emulsion obtained was cooled to 40° C. while stirring. Component (13) was added to the emulsion and homogeneously mixed. The mixture was cooled by a heat-exchanger finally to 30° C. to prepare a cold cream.

The cold cream thus obtained exhibited excellent moistened and decent feel without sliminess, providing an excellent moisture-retention effect and fresh feel upon use.

Example 6

Cream-type Moisturizing Foundation

A cream-type moisturizing foundation having the following formulation was prepared according to the process explained below.

| <Formulation> | % by weight |
| --- | --- |
| (1) Abietane | 10.0 |
| (2) Liquid paraffin | 8.0 |
| (3) Squalane | 8.0 |
| (4) Neopentyl glycol dioctanate | 3.0 |
| (5) Sorbitan sesquiisostearate | 7.0 |
| (6) Aluminum distearate | 0.2 |
| (7) Magnesium sulfate | 0.7 |
| (8) Maltitol | 2.0 |
| (9) Glycerol | 3.0 |
| (10) Methyl parabene | 0.1 |
| (11) Titanium oxide | 8.0 |
| (12) Talc | 5.0 |
| (13) Sericite | 2.0 |
| (14) Red iron | 0.4 |
| (15) Yellow iron | 0.7 |
| (16) Black iron | 0.1 |
| (17) Perfume | q.s. |
| (18) Purified water | Balance |
| Total | 100.0 |

Preparation Method

Into components (1)–(6) heated to 70° C. and homogeneously mixed, components (11)–(16) were dispersed. To this mixture was gradually added a homogeneous mixture of components (7)–(10) and (18) while stirring to prepare an emulsion. The emulsion was cooled with stirring to 40° C., component (17) was added at that temperature and further cooled with stirring to room temperature to obtain a creamy foundation.

The creamy foundation exhibited excellent moistened and decent feel without sliminess, providing an excellent moisture-retention effect and fresh feel upon use.

Example 7

Moisturizing Lipstick

A lipstick having the following formulation was prepared according to the process explained below.

| <Formulation> | % by weight |
| --- | --- |
| (1) Norabietane | 20.0 |
| (2) Abietane | 5.0 |
| (3) Carnauba wax | 2.0 |
| (4) Ceresine | 4.0 |
| (5) Candelilla wax | 5.0 |
| (6) Microcrystalline wax | 2.0 |
| (7) Bees wax | 5.0 |
| (8) Lanolin | 4.0 |
| (9) Castor oil | 20.0 |
| (10) Hexadecyl alcohol | 20.0 |
| (11) Glycerol | 3.0 |

| <Formulation> | % by weight |
|---|---|
| (12) Glycerol monostearate | 2.0 |
| (13) Titanium oxide | 2.0 |
| (14) Pigment (Red No. 202) | 2.0 |
| (15) Pigment (Red No. 204) | 1.0 |
| (16) Pigment (Yellow No. 4 Al lake) | 3.0 |
| (17) Antioxidant | q.s. |
| (18) Perfume | q.s. |
| Total | 100.0 |

Preparation Method

To components (1)–(8), (10), and (12) dissolved with heating, component (11) was added dropwise with stirring and components (13)–(18) dispersed in component (9) were further added. The mixture was homogeneously mixed with stirring and charged into a mold followed by cooling to prepare a lipstick.

The lipstick exhibited excellent moistened feel without sliminess, providing an excellent moisture-retention effect and fresh feel upon use.

Example 8

Nailenamel Remover

A nailenamel remover having the following formulation was prepared according to the process explained below.

| <Formulation> | % by weight |
|---|---|
| (1) Acetone | 60.0 |
| (2) Butyl acetate | 30.0 |
| (3) 1,3-butanediol | 2.0 |
| (4) Norabietane | 1.0 |
| (5) Dye | q.s. |
| (6) Perfume | q.s. |
| (7) Purified water | Balance |
| Total | 100.0 |

Preparation Method

Components (1)–(7) were homogeneously mixed to prepare a nailenamel remover.

The nailenamel remover had an excellent feel upon use.

Obviously, numerous modifications and variations of the present invention are possible in light of the above teachings. It is therefore to be understood that the scope of the appended claims, the invention may be practiced otherwise than a specifically described herein.

What is claimed is:

1. An oily composition for external application comprising a tricyclic saturated hydrocarbon represented by the following formula (I):

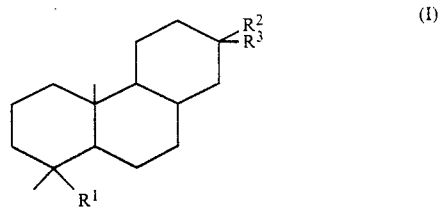

wherein $R^1$ and $R^2$ may be the same or different and independently represents a hydrogen atom or a methyl group and $R^3$ represents an alkyl group having 2–3 carbon atoms, and other carriers acceptable for external application.

* * * * *